United States Patent [19]

Shichman

[11] Patent Number: 5,011,487
[45] Date of Patent: Apr. 30, 1991

[54] VASCULAR CLAMP ASSEMBLY

[75] Inventor: Daniel Shichman, Trumbull, Conn.

[73] Assignee: United States Surgical Corporation, Norwalk, Conn.

[21] Appl. No.: 65,781

[22] Filed: Jun. 24, 1987

[51] Int. Cl.5 .............................................. A61B 17/2
[52] U.S. Cl. .................................. 606/158; 606/208; 24/516
[58] Field of Search ....................... 128/326, 325, 346; 251/9; 24/516, 515, 503, 504, 506, 517, 543, 544; 606/158, 157, 205, 206, 208

[56] References Cited

U.S. PATENT DOCUMENTS

| | | |
|---|---|---|
| 717,367 | 12/1902 | Ellis .......................................... 24/517 |
| 2,202,352 | 5/1940 | McGugin .............................. 24/506 |
| 3,326,217 | 6/1967 | Kerr ...................................... 129/325 |
| 4,165,747 | 8/1979 | Bermant . |
| 4,291,698 | 9/1981 | Fuchs ................................. 24/543 X |
| 4,337,774 | 7/1982 | Perlin . |
| 4,630,608 | 12/1986 | Arroyo . |
| 4,671,281 | 6/1987 | Beroff et al. ......................... 128/346 |
| 4,681,109 | 7/1987 | Arroyo ............................ 128/346 X |

OTHER PUBLICATIONS

Journal of Microsurgery, vol. 3, Winter Issue, A Variable-Force Microvascular Clip, pp. 89–91.
Plastic and Reconstructive Surgery, 1979, vol. 63, No. 6, A New Clamp for Microvascular Anastomoses, pp. 855–857.
Neurosurgery, vol. 5, No. 4, 1979, Temporary Microvascular Clips, pp. 456–463.
Plastic and Reconstructive Microsurgery, pp. 30–33.
Journal of Microsurgery, Fall, 1981, A New Microvascular Surgical Clip System, pp. 28–31.

*Primary Examiner*—Michael H. Thaler
*Attorney, Agent, or Firm*—Thomas R. Bremer; Peter G. Dilworth; Rocco S. Barrese

[57] ABSTRACT

A vascular clamp assembly includes a peripheral frame having an open central area, a support bar mounted on the frame, and a pair of clamps that are slidably mounted on the support bar. Each clamp includes an upper jaw member, a lower jaw member and a tension adjustor plate. The upper jaw member is pivotally mounted on the lower jaw member in a longitudinally overlying relationship with the lower jaw member. The tension adjustor plate is pivotally mounted to the lower jaw member and slidably engageable with the upper jaw member so that the plate may be wedged between the upper and lower jaw members in selectable positions. Each clamp also includes a pair of blades which are disposed in overlying relationship and which are relatively positionable, in accordance with the position of the tension adjustor plate, so that they can receive between them and engage a blood vessel and exert on the vessel a selectable holding force.

16 Claims, 3 Drawing Sheets

VASCULAR CLAMP ASSEMBLY

BACKGROUND OF THE INVENTION

1. Field of the Invention

This invention relates to a vascular clamp assembly, and more particularly relates to an adjustable, variable closure force microvascular clamp.

2. Description of the Prior Art

For years, surgeons and others have strived to design the ideal microvascular clamp for temporary vascular occlusion. Such a clamp should be easy to apply to the vessel, atraumatic and have a closing pressure that is sufficient to prevent bleeding and accidental displacement—in other words, a clamp that can occlude the vessel without crushing it.

Conventional surgical clamps for temporary occlusion come in a variety of configurations, and are either the adjustable type, having a variable closing pressure, or the pre-fixed type, having a closure force set by the manufacturer. Each type has its disadvantages.

Logistical problems are often encountered in the operating room when the surgeon elects to perform vascular surgery using the latter, pre-fixed type of clamp, as the operating room must be outfitted, preparatory to surgery, with a vast array of clamps, graduated in size and closure force.

Furthermore, the selection of the proper clamp is quite subjective, even if its closure force is known. Oftentimes, the gradation in available clamp sizes and manufacturer set tensions does not accommodate the surgeon's immediate needs, and he may be forced to choose between an excessively strong or oversized clamp, which may severely injure the blood vessel, and an undersized clamp with insufficient closure force, which may slip from the vessel or not provide the desired vascular occlusion.

For these reasons, many surgeons prefer to use clamps with an adjustable closure force.

One often used adjustable type clamp, commonly referred to as the Henderson clamp-approximator, basically consists of two clamps interconnected by a sliding tube system. Each clamp includes overlying blades between which the vessel is received. The blades apply an adjustable clamping force to the vessel that is regulated by a cylindrical key.

Although suitable for many applications, the Henderson clamp-approximator has a number of disadvantages. First, the closing pressure of the clamps cannot be finely adjusted, and the surgeon may inadvertently crush small vessels with this device.

Second, the Henderson apparatus is difficult to apply, as the surgeon must hold the clamp in one hand, the adjustment key in the other, and maneuver the vessel between the blades with a third hand.

Third, the need to screw the clamps shut rather than clip them onto the vessel makes the Henderson clamp-approximator awkward to use.

Another microvascular surgical clip having an adjustable, variable closure force is described in the Journal of Microsurgery, Volume 3, Winter Issue, 1981, pages 89-91. The clip includes a resilient annular body which extends into a pair of cooperating, vessel engaging blades. A narrow channel with three enlargements is formed in the annular body of the clip. A spring is secured at one of its ends to the inner surface of the annular body on the opposite side of the channel, and extends across the interbody space, where its other end is secured to an adjustable pin slidably mounted within the channel. The spring's tension is adjusted by moving the pin into the various enlargements of the channel. Adjustment of the spring affects the closure force of the blades.

The device described above is disadvantageous to use because the coiled spring is likely to accumulate clotted blood, much more so than with other types of clamps. The clotted blood is difficult to remove, and may affect the resilience of the clip and its closure force.

A further microsurgical clip is disclosed in U.S. Pat. No. 4,337,774, which issued to Alfred Perlin. Perlin describes in his patent a surgical clip design having a pair of integrally joined arms, each of which terminate in a flat jaw. The arms are formed of springy material and are outwardly sprung. The first arm includes a cam track formed with a number of detents on its outer surface. A resilient rod is mounted cantilever-fashion on the second arm, and has a cam follower at its end which rides on the cam track to bring the jaws into a desired degree of clamping force with a blood vessel.

The Perlin clip disclosed in the above-identified U.S. patent is suitable for use in many applications, although, like other conventional clamps described previously, presents a number of disadvantages in its use. One major disadvantage is that the cam track formed on one of the arms is exposed. The detents formed in the cam track may accumulate blood which may not only affect the closure force of the clip, but also prevent the cam follower from properly engaging the detent. The cam follower may in fact slip out of the selected detent and into an undesired location on the cam track, which may affect the closure pressure of the vessel holding jaws.

Additionally, the cam follower extends considerably beyond the interior area of the clip. The cam follower thus remains exposed and unprotected. Because of the confined space in which to work, the surgeon may inadvertently dislodge the cam follower from its selected detent which of course may increase or decrease the closure force of the jaws on the vessel.

OBJECTS AND SUMMARY OF THE INVENTION

It is an object of the present invention to provide an adjustable, variable closure force microvascular clamp.

It is another object of the invention to provide an adjustable microvascular clamp that is easily and readily adjustable by finger pressure and which requires no further instrument to set.

It is still another object of the invention to provide an adjustable microvascular clamp which protects the mechanism for adjusting the closure force from inadvertent slippage.

It is yet a further object of the invention to provide an adjustable clamp assembly which is adaptable to a variety of surgical clamping uses and applications and which can be readily modified by the surgeon for such applications.

It is yet another object of the present invention to provide an adjustable microvascular clamp which is mechanically simple in construction and easy to manufacture.

It is an additional object of the invention to provide a vascular clamp assembly which overcomes the inherent disadvantages of known clamp assemblies.

In accordance with one embodiment of the present invention, a vascular clamp includes first and second elongate members that are operatively coupled together. Each of the first and second members includes a blood vessel engaging surface. The vessel engaging surfaces are disposed in overlying relationship, and they are relatively positionable so that they can receive between them and engage a blood vessel, and exert on the vessel a selectable holding force.

The vascular clamp of the present invention further includes an adjustment mechanism for effecting the relative positioning of the elongate members' vessel engaging surfaces, and for adjusting the holding force exerted by the surfaces on the blood vessel. The adjustment mechanism includes a substantially non-compressible third member at least partially interposed, cantilever fashion, between the first and second members. The third member is pivotally mounted at one of its ends to the first member, and slidably engageable with the second member. Thus, the third member is adapted to be wedged between the first and second members in selectable positions. This affects the relative positioning of the vessel engaging surfaces of the elongate members and the holding force exerted by the members on the vessel.

In another form of the invention, a vascular clamp assembly includes a pair of clamps, each generally having the structure described above, slidably mounted on a support bar. The bar is removably mounted across a closed loop, peripheral frame member. The frame member is provided to aid the surgeon in the suturing operation.

Preferred forms of the vascular clamp assembly, as well as other objects, features and advantages of this invention, will become apparent from the following detailed description of illustrative embodiments thereof, which is to be read in connection with the accompanying drawings.

DETAILED DESCRIPTION OF THE PREFERRED EMBODIMENTS

Figure 1:
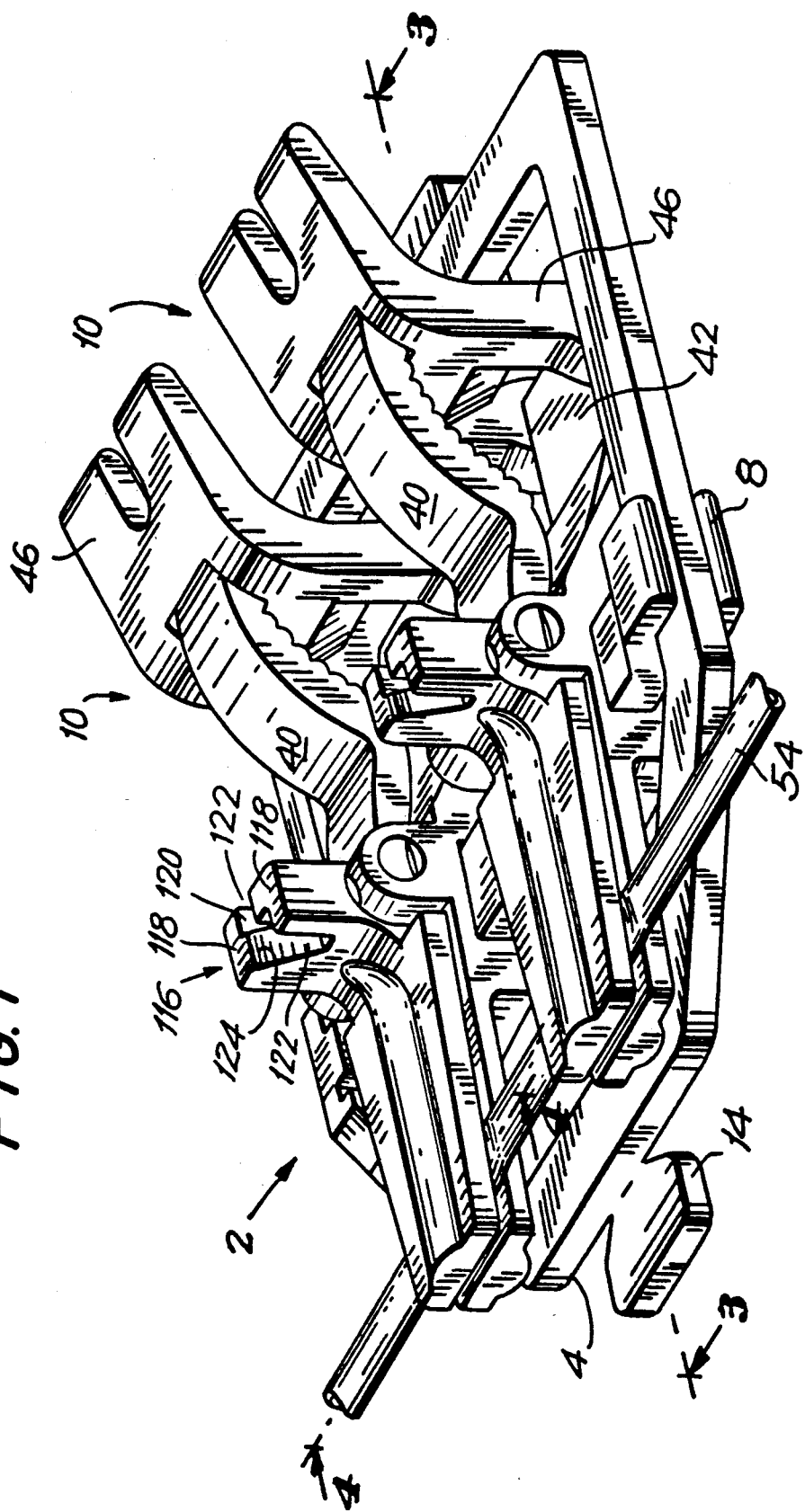
FIG. 1 is a perspective view of one form of the microvascular clamp assembly of the present invention.

Referring now to the drawings, it can be seen that a microvascular clamp assembly 2, constructed in accordance with the present invention, includes a peripheral frame 4 having an open central area 6, a support bar mounted 8 on the frame 4, and a pair of clamps 10 that are slidably mounted on the support bar 8.

The frame 4 is a closed loop of resilient material in the form of a six-sided polygon. The frame 4 includes at least two opposite sides 12 which are parallel to each other, which serve as supports for the clamp support bar 8 mounted transversely between them.

The frame 4 is further provided with a front tab 14 and a rear tab 16, which are mounted opposite one another on the frame 4. During an operation, the surgeon may temporarily tie the sutures to the frame by looping them around the front or rear tabs 14, 16.

The two parallel opposite sides 12 of the frame are modified to accommodate the clamp support bar 8. A recess 18 is formed in the inner surface of one side 12. Aligned directly across from the recess 18 in the other opposite side 12 is a receptacle 20, which is formed in a widened portion 22 of the side. The receptacle 20 includes an upper tab 24, and a pair of lower, inwardly directed shoulders 26.

The clamp support bar 8 is an elongated member which is designed to be removably mounted on the frame 4 between the receptacle 20 and the recess 18 formed in the opposite parallel sides 12. It is preferably rectilinear in its transverse cross sectional shape, which helps prevent the clamps 10 from twisting on the bar during use. The bar 8 may include a rib 27 formed on one of the lateral sides of the bar and extending along its length.

The clamp support bar 8 includes one end 28 which is forked to form two parallel, spaced apart arms 30 that are separated by a distance substantially equal to the thickness of the frame side 12 having the recess 18. The other opposite end 32 of the clamp support bar 8 includes a narrowed tip 34, defining shoulders 36 on opposite sides of the tip.

The forked end 28 of the bar is seated in the recess 18 with its arms straddling the frame's side 12, and the tip portion 34 of the bar is received by the receptacle 20 formed in the other side 12, and held resiliently in place by the upper tab 24 and lower shoulders 26 of the frame 4. The clamp support bar 8 can be easily removed from the frame 4 by distorting the frame slightly and dislodging the narrowed tip 34 from the frame receptacle 20.

The preferred form of the clamp assembly 2 of the present invention includes a pair of clamps 10 slidably mounted on the clamp support bar 8. The clamps 10 may be adjusted by the surgeon on the bar 8 to provide whatever spacing is required between clamps. Also, each clamp 10 may be removed from the rest of the assembly for individual use by removing the bar 8 from the frame 4 and sliding the clamp 10 over the tipped end 34 of the bar.

Each clamp 10 of the assembly is identical in structure and basically includes three components: an upper jaw member 40, a lower jaw member 42 and a tension adjustor plate 44.

The upper jaw member 40 is generally in the form of an elongated, substantially flattened structure. It includes a central mounting portion 46, provided with a pair of pins 48 projecting from opposite sides, for mounting the upper jaw member 40 on the lower jaw member 42. As will be seen, the lower half portion of each pin's axial ends is beveled to facilitate mounting the upper jaw member 40 on the lower jaw member 42.

The front portion 50 of the upper jaw member 40 includes a flattened, plate-like blade 52 extending from the central mounting portion 46. The blade 52 is designed to receive and hold a blood vessel 54 between it and a similar blade formed on the lower jaw member 42.

The rear portion 56 of the upper jaw member 40 extends from the central mounting portion 46 diametrically opposite the front blade 52, and is preferably formed with a free standing, curved end 58. The lower surface of this curved end 58 is knurled to form a plurality of parallel ridges 60.

The lower jaw member 42 has a structure which is substantially complementary to the upper jaw member 40. It also includes a central mounting portion 62, which cooperates with the mounting portion 46 of the upper jaw member 40, and front and rear portions 64, 66 which extend from diametrical opposite sides of the central mounting portion 62.

The front portion 64 of the lower jaw member 42 is formed with a plate-like blade 68, which conforms in shape and dimensions to the blade 52 of the upper jaw member 40. When the clamp 10 is assembled, the blades 52, 68 overlie each other and, as will be seen, pivot with respect to one another to open and close upon a blood vessel 54.

The central mounting portion 62 of the lower jaw member 42 includes a pair of upstanding projections 70 formed on its upper surface. The projections 70 are spaced apart a distance sufficient to receive the central mounting portion 46 of the upper jaw member 40 between them. Each projection 70 includes a bore 72 formed through its thickness, which bores receive the mounting pins 48 of the upper jaw member 40. To facilitate assemblage, the inside facing surfaces 74 of the projections 70 are obliquely countersunk to allow the mounting pins 48 of the upper jaw member 40 to be snap-fitted therebetween and received by their respective bores 72.

The rear portion 66 of the lower jaw member 42 includes a pair of mounting pins 76 positioned about halfway along the rear portion's length and projecting outwardly from opposite sides of the member 42. These pins 76 are used for mounting the tension adjustor plate 44 to the lower jaw member 42.

As mentioned previously, each clamp 10 is slidably mounted on the clamp support bar 8. A mounting opening 80 is formed entirely through the body of the lower jaw member 42, the shape of which conforms closely to the transverse cross sectional shape of the clamp support bar 8. Two "L" shaped arms 82 in mirror image disposition define the mounting opening 80, and are separated by a slot 84 to provide some resiliency to the arms 82. This facilitates the ability of the clamps 10 to freely slide on the clamp support bar 8, and yet maintain their position on the bar when set by the surgeon.

Furthermore, the lower jaw member's length may be selected to allow its front and rear portions 64, 66 to overlap the frame 4, above and below the upper and lower surfaces of the frame 4. This further prevents the clamps 10 from twisting on the support bar 8 and helps maintain their set position.

The upper jaw member 40 is longitudinally overlyingly mounted on the lower jaw member 42, and pivots thereon in a rocker or seesaw fashion. The overlying relationship of the two jaw members 40, 42, and their blades 52, 68, allow the blades to engage a blood vessel 54 between them.

Figure 2:
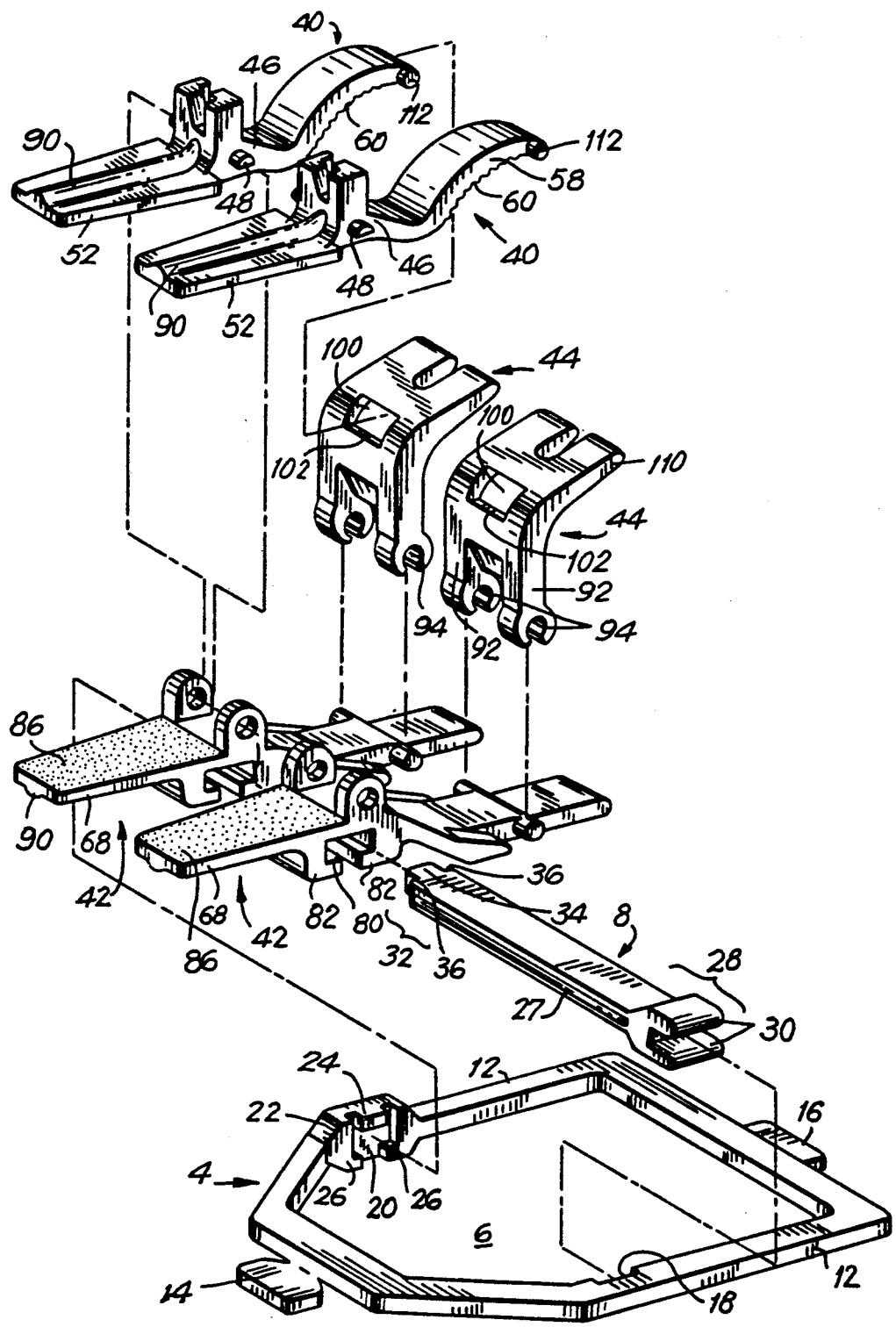
FIG. 2 is an exploded view of the assembly illustrated by FIG. 1.

The blade portions 52, 68 of each jaw member are preferably provided with vessel engaging surfaces 86, which constitute the lower and upper surfaces of the upper jaw member's and lower jaw member's blades, respectively. The vessel engaging surfaces 86 of each blade 52, 68 are substantially flat. However, the surfaces may be randomly textured, as shown in FIG. 2, with the texturing being between about 0.001 and 0.003 inches in depth, to improve the clamps holding ability on the blood vessel 54 and to minimize slippage from the vessel.

The vessel engaging surfaces 86 of each jaw's blade is also preferably flat to distribute the closure forces of the clamp evenly over the entire area of the surface 86; this further minimizes the atraumatic affects of the clamp 10 on the blood vessel 54. If desired, the blade of each jaw member 40, 42 may be made especially thin, and a stiffener rib 90 extending longitudinally over the upper surface of the upper jaw member 40 and the lower surface of the lower jaw member 42 may be provided to help strengthen the blades 52, 68.

As mentioned previously, each clamp 10 includes a tension adjustor plate 44. The plate 44 is preferably mounted pivotally to the lower jaw member 42 and wedged cantilever fashion between the lower jaw member 42 and the upper jaw member 40.

The tension adjustor plate 44 is substantially a non-compressible, plate-like member. It includes one end that is formed with a pair of parallel, free-standing arms 92. Each arm 92 has a bore 94 formed through its thickness. The free-standing arms 92 are spaced apart a distance which is substantially equal to the width of the rear portion 66 of the lower jaw member 42. The ends of each free-standing arm 92 may be slotted and slightly resilient so that they can be easily deformed and snap-fitted onto the pair of mounting pins 76 provided on the lower jaw member's rear portion 66. When the clamp 10 is assembled, the tension adjustor plate 44, mounted on the lower jaw member 42, pivots about the mounting pins 76 between the upper and lower jaw members 40, 42, the mounting pins 76 of the jaw member 42 and bores 94 of the plate 44 defining the axis of pivot.

In its preferred form, the tension adjustor plate 44 includes a central opening 100 formed through its thickness. The dimensions of the central opening 100 are chosen so that the rear portion 56 of the upper jaw member 40 may be received by and be freely movable within the opening 100.

The lowermost extent of the central opening 100 is defined by a contact edge 102 having a thickness of between about 0.003 and 0.005 inches. When the clamp 10 is assembled, this edge 102 engages the knurled lower surface of the upper jaw member 40.

The contact edge 102 of the central opening 100 is spaced from the pivotal axis of the adjustor plate's lower end a distance which is greater than the distance between the pivotal axis and any point on the knurled lower surface of the upper jaw member 40, when the clamp 10 is assembled as shown in FIG. 1. This allows the adjustor plate 44 to be wedged between the rear portions 56, 66 of the upper and lower jaw members 40, 42, with its contact edge 102 engaging the knurled lower surface of the upper jaw member 40.

Figure 3:
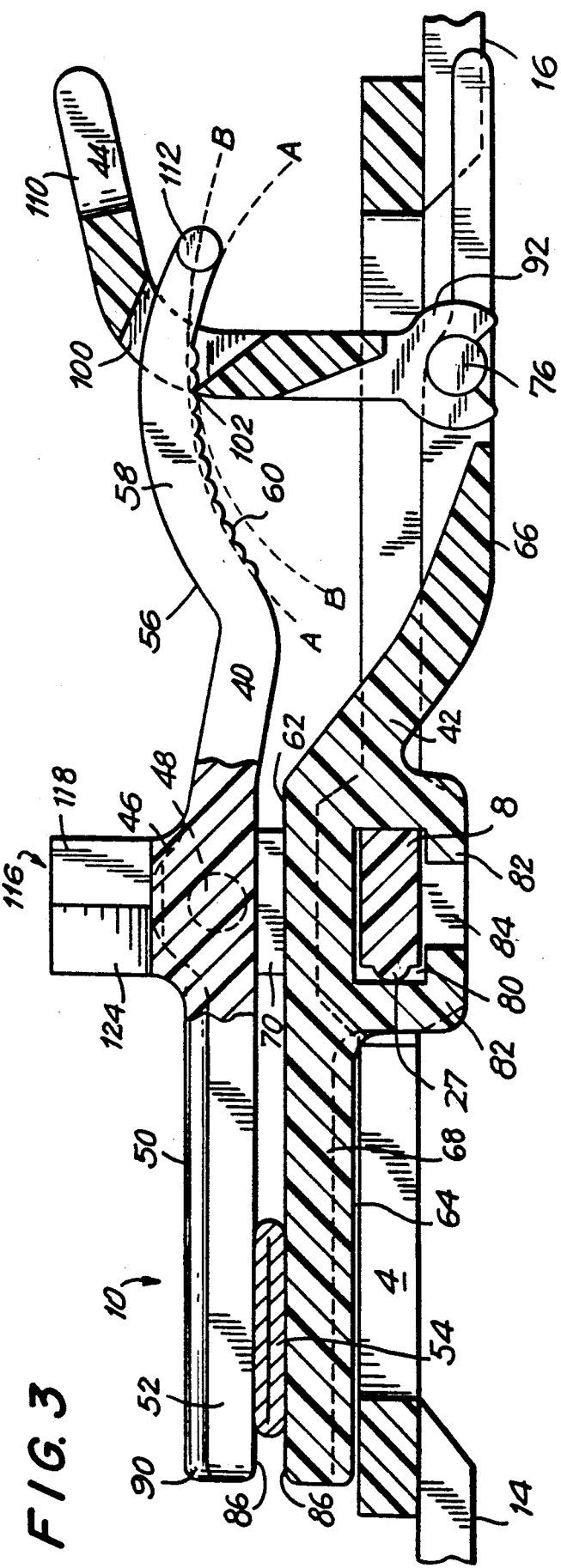
FIG. 3 is a partial sectional view of the assembly shown in FIG. 1, taken along the line 3—3 of FIG. 1.

When the blade engaging surfaces 86 of the upper and lower jaw members 40, 42 are clamped onto a blood vessel 54 of a particular size, the curved rear portion 56 of the upper jaw member 40 circumscribes a particular arc (illustrated by broken line A—A in FIG. 3) with respect to the pivotal axis of the adjustor plate 44. This arc is eccentric to the pivotal axis, the more rearward portion of the member 40 bearing closer to the pivotal axis.

The contact edge 102 of the adjustor plate 44 also circumscribes an arc (illustrated by broken line B—B) in its swing about the pivotal axis. However, this arc is concentric about the pivotal axis (radially equi-distant at all points). The two arcs intersect at a single point, and diverge forwardly and rearwardly of that point. Because of the overlying, rocker style mounting of the two jaw members 40, 42, any deflection of the upper jaw member's rear portion 56 caused by wedging the adjustor plate 44 between the two jaw members has a reciprocal affect on the relative positions of the blades 52, 68 and the force which the blades exert on the vessel 54.

Figure 4:
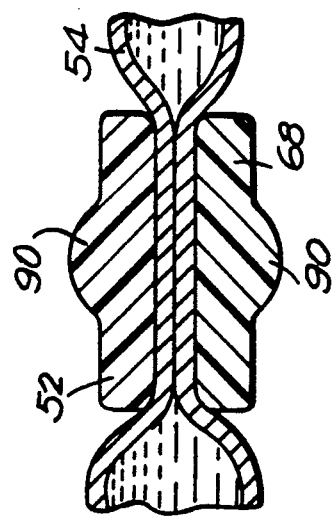
FIG. 4 is a sectional view of one of the clamps of the assembly shown in FIG. 1, taken along the line 4—4 of FIG. 1.

Thus, the contact edge 102 does not engage the upper jaw member 40 when the adjustor plate 44 is pivoted forwardly on the clamp 10, so that the jaw blades 52, 68 are free to open; and engages the upper jaw member 40 with increasing force as the adjustor plate 44 is pivoted more rearwardly on the clamp 10, which causes the blades 52, 68 to close about the vessel 54 with increasing pressure to constrict the flow of blood through the vessel, as illustrated by FIG. 4.

The upper end portion 110 of the tension adjustor plate 44 may extend beyond the upper surface of the upper jaw member 40 to allow the surgeon to easily grasp the tension adjustor plate 44 with an instrument or his finger to maneuver the plate to various positions between the upper and lower jaw members 40, 42. This portion is preferably angled with respect to the remaining plate portion underlying the upper jaw member 40 such that the end 110 of the adjustor plate 44 stands upright (substantially perpendicular to the upper jaw member 40) when the plate 44 is in its most forward position, so that it can be grasped by the surgeon.

Each clamp 10 may also include a stop projection 112 formed on the end of its upper jaw member's rear portion 56. The stop projection 112 protrudes from a side of the upper jaw member 40, and abuts against the adjustor plate 44 when the plate is in its most rearward position. This keeps the upper jaw member 40 within the central opening 100 of the adjustor plate 44, and limits the pivotal swing of the plate 44.

In a further preferred form, each clamp 10 may be provided with a suture tie post 116. The tie post 116 is integrally formed with the upper jaw member 40 and situated to project upwardly from the top of the upper jaw member's central mounting portion 46.

The tie post 116 basically includes two L-shaped members 118 situated adjacent to each other transversely on the jaw member. Each member 118 is oriented 180° reverse to the other, and both are spaced apart to define a suture receiving slot 120 between them, which slot is open at the top of the tie post 116.

The receiving slot 120 follows a tortuous path through the post between two misaligned slot openings 122 formed in the front and rear sides of the post. An inner side wall 124 of each L-shaped member 118 may be sloped to converge with the other member near the bottom of the post 116 so as to provide a wedge shape to each slot opening 122.

The tie post 116 may be used by the surgeon for temporarily holding the suture, the suture being wedged into the receiving slot 120 formed in the post. The post 116 may also serve as a leverage point when tweezers are used between the post and the tension adjustor plate 44 to open or close the clamp.

The vascular clamp assembly 2 of the present invention is used by positioning the blood vessel 54 between the cooperating blades 52, 68 of the clamps 10. Tension on the blades 52, 68 is released by pivoting the adjustor plates 44 to their most forward position. The clamps 10 are also adjusted in their position on the clamp support bar 8 to provide the spacing between each clamp that is required by the surgeon.

After the blood vessel is properly positioned within the blades 52, 68 of the clamps, the surgeon maneuvers the adjustor plates 44 rearwardly with respect to the clamps to increase the holding force that the clamp blades exert on the blood vessel 54. The contact edge 102 of the adjustor plate's central opening 100 is held in place between adjacent ridges 60 of the upper jaw member's knurled lower surface so that proper pressure on the blood vessel 54 is maintained.

The vascular clamp assembly 2 of the present invention is a mechanically simple device and easy to manufacture, as each clamp 10 includes only three components. It is manufactured in a series of sizes, each size provided to accommodate vessels within a particular diameter range. For example, one size is designed for vessels having a diameter of between 0.7 mm and 1.75 mm, and provides an adjustable closure force of between 0 and 250 grams.

Furthermore, the dual clamp assembly may be used in the configuration shown at FIG. 1, or may be readily disassembled by the surgeon if only the individual clamps are required, making the assembly adaptable to many applications.

Additionally, the tension adjustment mechanism of each clamp, comprising the contact edge 102 of the adjustor plate 44 and the knurled end of the upper jaw member 40, is protected from an accumulation of blood and accidental dislodgement by being disposed between the jaw members 40, 42.

The various components of the clamp assembly 2 may be formed from various metals, such as stainless steel or die-cast aluminum, or from plastics, such as bio-degradable, absorbable or non-absorbable resins, for example, those prepared from glycolides and/or lactides.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A vascular clamp assembly, which comprises:
   first and second elongate members pivotally mounted together at a common pivot point, each of the first and second members including first and second end portions extending in opposite directions from the common pivot point, the first end portion of each member defining a vessel engaging surface, the vessel engaging surfaces being relatively positionable to receive therebetween and engage a blood vessel and to exert on the vessel a selectable holding force; and
   a tension adjustor member at least partially interposed between and transversely disposed to the second end portions of the first and second members, the tension adjustor member having a first end pivotally mounted on the second end portion of the second member, and a contact edge spaced from the pivotal first end and slidably engagable with the second end portion of the first member over an edge engaging surface thereof wherein the second end portion of the first member is curved over at least a portion of said edge engaging surface, the distance between the pivotal axis of the first end and the contact edge being greater than the distance between the pivotal axis of the first end and the edge engaging surface of the first member along a portion of the edge engaging surface to allow the tension adjustor member to be wedged between the second end portions of the first and second members in selectable positions with respect to the edge engaging surface, thereby effecting a positioning between the first end portions of the first and second members.

2. A vascular clamp assembly as defined in claim 1, wherein the curvature of the second end portion of the first member defines an arc; and wherein pivotal movement of the adjustor member causes the contact edge to define an arc which is concentric to the pivotal axis of the first end of the adjustor member and intersects the arc defined by the first member.

3. A vascular clamp assembly as defined in claim 1, wherein the tension adjustor member includes a second end portion disposed opposite the pivotal first end and outwardly of the first member.

4. A vascular clamp assembly as defined by claim 3, wherein the second end portion of the tension adjustor member forms an angle with that portion of the tension adjustor member extending between the first and second members.

5. A vascular clamp assembly as defined by claim 3, wherein the tension adjustor member includes an opening.

6. A vascular clamp assembly as defined by claim 5, wherein the second end portion of the first member includes a stop projection formed thereon, the stop projection protruding from a side of the first member.

7. A vascular clamp assembly as defined by claim 1, wherein the edge engaging surface of the first member is formed to define means for maintaining the adjustor member in a selected position.

8. A vascular clamp assembly as defined by claim 7, wherein the position maintaining means includes a plurality of parallel ridges, the contact edge of the tension adjustor member being adapted to contact the edge engaging surface between adjacent ridges.

9. A vascular clamp assembly as defined by claim 1, wherein the second elongate member further includes means for mounting the first elongate member thereon, the first member mounting means including a pair of upstanding, spaced apart projections protruding therefrom, each projection having a bore formed therein; and wherein the first elongate member includes a pair of first mounting pins projecting from opposite sides thereof, each pin being adapted to be received by a corresponding projection bore to allow the first member to be mounted between the projections.

10. A vascular clamp assembly as defined by claim 9, wherein the second member further comprises means for mounting the tension adjustor member, the tension adjustor mounting means including a pair of second mounting pins projecting from opposite sides thereof; and wherein the pivotal first end of the tension adjustor member includes a pair of free standing, parallel arms, each arm including a bore formed therein and positioned to receive a corresponding second mounting pin.

11. A vascular clamp assembly as defined by claim 1, which further comprises a clamp support bar, the second elongate member being transversely mounted on the support bar and slidable thereon.

12. A vascular clamp assembly as defined by claim 11, which further comprises a peripheral frame defining an open central area, the support bar being mounted on the frame.

13. A vascular clamp assembly as defined by claim 1, wherein the vessel engaging surfaces of the first and second members are textured to minimize slippage of a vessel held therebetween.

14. A vascular clamp assembly as defined by claim 1, wherein at least one of the first and elongate members includes a post projecting therefrom, the post having a slot formed therein.

15. A vascular clamp assembly as defined by claim 14, wherein the post includes a pair of L-shaped members situated adjacent to each other and transversely on the elongate member, the L-shaped members being spaced apart to define the post slot between them.

16. A vascular clamp assembly as defined by claim 15, wherein each L-shaped member is disposed on the jaw member in 180° reverse orientation to the other so as to provide the slot with a tortuous configuration through the post.

* * * * *